United States Patent
Eaker et al.

(12)

(10) Patent No.: US 6,276,873 B1
(45) Date of Patent: Aug. 21, 2001

(54) GROUND WATER REMEDIATION CONTROL PROCESS

(75) Inventors: Craig L. Eaker, Alta Loma; Randy S. Weidner, Thousand Oaks; Terry C. Sciarrotta, Rancho Santa Margarita; George M. Becker, Los Angeles, all of CA (US)

(73) Assignee: Southern California Edison Company, Rosemead, CA (US)

( * ) Notice: Subject to any disclaimer, the term of this patent is extended or adjusted under 35 U.S.C. 154(b) by 0 days.

(21) Appl. No.: 09/239,574

(22) Filed: Jan. 29, 1999

(51) Int. Cl.$^7$ .................................................. E21B 49/00
(52) U.S. Cl. .......................................... 405/131; 405/130
(58) Field of Search ..................................... 210/741, 170; 166/266, 272.5, 272.3, 250.01, 252.1, 303, 250, 272; 588/260, 250, 19; 405/131, 128

(56) References Cited

U.S. PATENT DOCUMENTS

| | | |
|---|---|---|
| 4,158,957 | 6/1979 | Deans et al. . |
| 4,273,187 | 6/1981 | Satter et al. . |
| 4,429,581 * | 2/1984 | Furmaga ............................ 73/861.04 |
| 4,441,362 * | 4/1984 | Carlson .................................... 73/155 |
| 4,615,390 | 10/1986 | Lucas et al. . |
| 4,815,536 * | 3/1989 | Prendergast et al. ................. 166/250 |
| 4,969,520 * | 11/1990 | Jan et al. .............................. 166/266 |
| 4,997,313 | 3/1991 | Gibson et al. . |
| 5,018,576 * | 5/1991 | Udell et al. ........................... 166/272 |
| 5,319,966 | 6/1994 | Jackson et al. . |
| 5,467,823 | 11/1995 | Babour et al. . |
| 5,520,046 | 5/1996 | Sornein et al. . |
| 5,520,483 | 5/1996 | Vigneri . |
| 5,577,558 | 11/1996 | Abdul et al. . |
| 5,615,974 * | 4/1997 | Land et al. ............................ 405/128 |
| 5,986,159 * | 11/1999 | Aines et al. ............................. 588/19 |
| 5,997,214 * | 12/1999 | De Rouffignac et al. ........... 405/128 |
| 6,033,577 * | 3/2000 | Braband et al. ...................... 210/741 |

* cited by examiner

Primary Examiner—Eileen D Lillis
Assistant Examiner—Raymond W Addie
(74) Attorney, Agent, or Firm—Sheldon & Mak; Denton L. Anderson

(57) ABSTRACT

A continuous process for removing organic contaminants from a subsurface formation. The process having the steps of: (a) treating the subsurface formation to mobilize the organic contaminants, such treating of the subsurface formation including withdrawing from the subsurface formation a liquid stream and a vapor stream, the liquid stream containing water, dissolved carbonaceous material and non-dissolved carbonaceous material, (b) separating the liquid stream into a first liquid stream component comprised substantially of water and soluble carbonaceous material and a second liquid stream component comprised substantially of non-soluble carbonaceous material, (c) testing the first liquid component stream to determine $C_d$, where $C_d$ is the amount of carbonaceous material in the first liquid stream component produced per unit of time by the treating of the subsurface formation in step (a), (d) testing the second liquid stream component to determine $C_n$, where $C_n$ is the amount of carbonaceous material in the second liquid stream component produced per unit of time by the treating of the subsurface formation in step (a), (e) testing the vapor stream to determine $C_v$, where $C_v$ is the amount of carbonaceous material in the vapor stream produced per unit of time by the treating of the subsurface formation in (a), (f) determining $C_g$, where $C_g$ is the quantity of carbonaceous materials in the vapor stream produced per unit of time by the treating of the subsurface formation in step (a), which is attributable to carbonaceous material in the subsurface formation other than the organic contaminants, (g) computing $C_c$, where $C_e = C_s + C_n + C_v - C_g$, and (h) controlling the treating of the subsurface formation in step (a) using $C_c$.

7 Claims, 2 Drawing Sheets

GROUND WATER REMEDIATION CONTROL PROCESS

FIELD OF THE INVENTION

Figure 1:
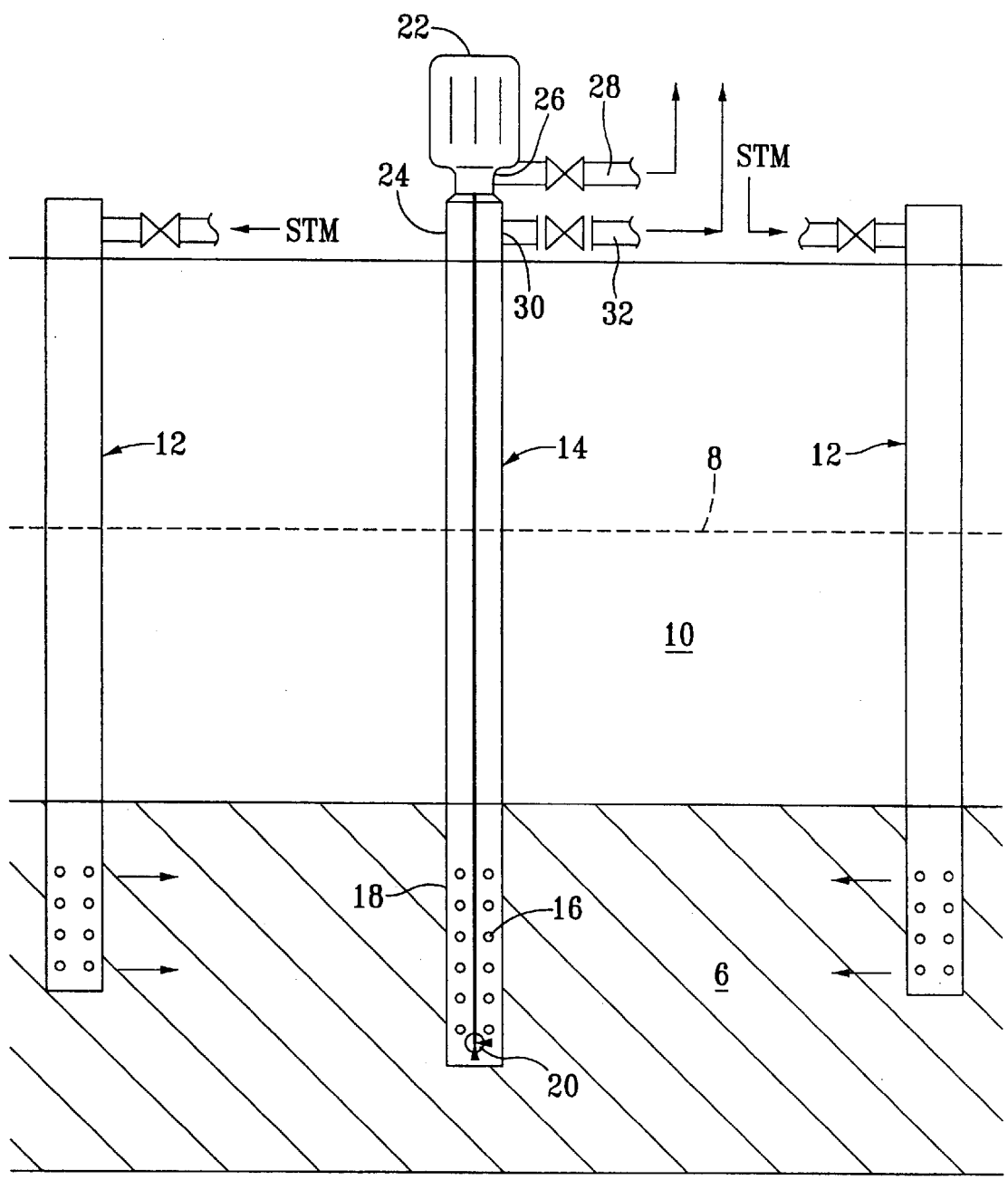

This invention relates generally to methods for removing organic contaminants from underground water formations and, specifically, to methods for controlling treatment methods used in removing contaminants from subsurface formations.

BACKGROUND OF THE INVENTION

The urgency of removing organic contaminants from underground water formations has become increasingly more apparent during the last three decades. This urgency has spawned a tremendous effort to improve ground water decontamination techniques.

Subsurface decontamination techniques fall into one of two broad classes, above-ground methods and in situ methods. Above-ground methods generally require the removal of contaminated soil and water from the subsurface formation, treatment of such soil and water in above-ground facilities, and re-introduction of the decontaminated soil and water into the subsurface formation. Above-ground methods have been found to be effective but extremely expensive, especially where the subsurface contamination is widespread.

For this reason, in situ methods are preferred whenever possible. In in situ methods, the contaminated zone within the subsurface formation is treated in situ by heating or by some other process to mobilize the contaminants. Once mobilized, the contaminants, in the form of contaminated liquids and vapors, are withdrawn from a contaminated zone via one or more extraction wells. The contaminated liquids and vapors are thereafter treated separately at above ground facilities.

One problem with such in situ methods is how to properly control the treatment process so as to maximize yields while minimizing costs. For many prior art in situ methods, the treatment process has been controlled by reference to the amount of non-soluble liquid contaminants extracted from the subsurface formation. This is especially true for in situ methods where the predominant contaminants are non-volatile heavy organic materials. The applicants have discovered, however, that such prior art control methods are based on erroneous assumptions and can lead to marked inefficiencies in the remediation process.

Accordingly, there is a need for an improved subsurface remediation process having greater efficiency than processes of the prior art.

SUMMARY

The invention satisfies this need. The invention is a continuous process for removing organic contaminants from a subsurface formation comprising the steps of:

(a) treating the subsurface formation to mobilize the organic contaminants, such treating of the subsurface formation including withdrawing from the subsurface formation a liquid stream and a vapor stream, the liquid stream containing water, dissolved carbonaceous material and non-dissolved carbonaceous material;

(b) separating the liquid stream into a first liquid stream component comprised substantially of water and soluble carbonaceous material and a second liquid stream component comprised substantially of non-soluble carbonaceous material;

(c) testing the first liquid component stream to determine $C_d$, where $C_d$ is the amount of carbonaceous material in the first liquid stream component produced per unit of time by the treating of the subsurface formation in step (a);

(d) testing the second liquid stream component to determine $C_n$, where $C_n$ is the amount of carbonaceous material in the second liquid stream component produced per unit of time by the treating of the subsurface formation in step (a);

(e) testing the vapor stream to determine $C_v$, where $C_v$ is the amount of carbonaceous material in the vapor stream produced per unit of time by the treating of the subsurface formation in (a);

(f) determining $C_g$, where $C_g$ is the quantity of carbonaceous materials in the vapor stream produced per unit of time by the treating of the subsurface formation in step (a), which is attributable to carbonaceous material in the subsurface formation other than the organic contaminants;

(g) computing $C_c$, where $C_c = C_d + C_n + C_v - C_g$; and (h) controlling the treating of the subsurface formation in step (a) using $C_c$.

In a typical embodiment, the treating of the subsurface formation is accomplished by heating a subsurface formation by the injection of steam. In this embodiment, the controlling of the treating of the subsurface formation largely entails the controlling of the input of steam to the subsurface formation so as to maximize the efficiency of the mobilization and removal of organic contaminants from the subsurface formation.

DRAWINGS

Figure 2:
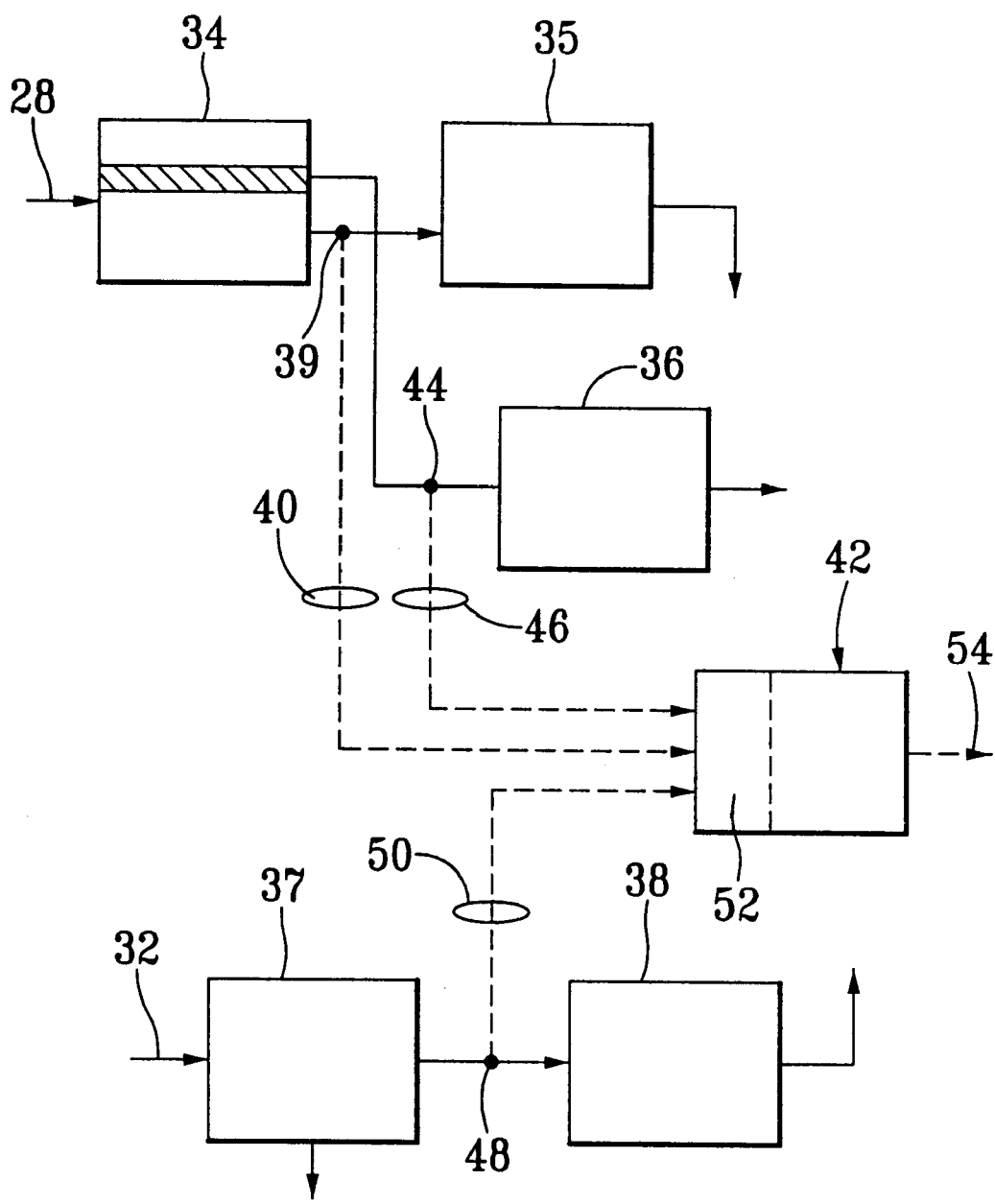

These features, aspects and advantages of the present invention will become better understood with regard to the following description, appended claims and accompanying figures where:

FIG. 1 is a diagrammatic view of apparatus used to remediate subsurface formations; and FIG. 2 is a diagrammatic view of apparatus used to remediate useful in the invention.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is an improved in situ process for removing organic contaminants from a subsurface formation wherein organic contaminants are mobilized in situ, and removed from the subsurface formation where they are divided into several separate streams. In the invention, the in situ process is controlled based upon a determination of the total yield of organic material from all of the several streams.

The process is best understood by reference to a typical example as illustrated in FIGS. 1 and 2. In FIG. 1, a contaminated zone 6 is located below the water line 8 within a subsurface formation 10. (It must be understood, however, that the method of the invention is operable for a wide variety of subsurface formations 10, including those which are water saturated and those which are not water saturated.) In the example, steam is injected into the contaminated zone 6 via one or more injection wells 12. Heat from the steam and, in some cases, pressure from the steam, mobilizes contaminated liquids and vapors within the contaminated zone 6 and induces those contaminated liquids and vapors to flow to one or more extraction wells 14. The contaminated vapors and liquids enter the extraction wells 14 via perforations 16 disposed in the lower ends 18 of the extraction wells 14. Liquids which accumulate in the lower ends 18 of the extraction wells 14 are pumped to the surface by pumps 20 disposed in the lower ends 18 of the extraction wells 14. The pumps 20 are typically powered by motors 22 disposed in the upper ends 24 of the extraction wells 14. Vapors which enter the lower ends 18 of the extraction wells 14 are swept upward to the surface by a differential pressure induced within the extraction wells 14 (typically by the application of a vacuum on the extraction wells 14 using a vacuum pump or other suitable equipment (not shown)).

At the upper ends 24 of the extraction wells 14, the contaminated liquids are removed from the extraction wells 14 at liquid discharge ports 26 and are carried away in one or more liquid discharge lines 28. Also at the upper ends 24 of the extraction wells 14, the contaminated vapors are removed from the extraction wells 14 via vapor discharge ports 30 and are carried away via one or more vapor discharge lines 32.

As illustrated in FIG. 2, the contaminated liquid stream removed from the extraction wells 14 to the liquid discharge lines 28 is first processed in extraction equipment 34 wherein the liquid stream is separated into a first liquid stream component, comprised substantially of water and soluble carbonaceous material, and a second liquid stream component, comprised substantially of non-soluble carbonaceous material. The first liquid stream component is thereafter treated in water treatment facilities 35, and the treated water is typically returned to the subsurface formation 10. The second liquid stream component can then be disposed of or it can be separately treated in oil treatment facilities 36 and then sold to refiners or chemical processors.

The vapor stream removed from the extraction wells 14 to the vapor discharge lines 32 is initially processed in condensation and separation equipment 37 wherein water vapor and entrained water droplets are coalesced for recycle, disposal or return to the subsurface formation 10. Downstream of the condensation and separation equipment 37, the non-condensible vapors are treated in vapor treatment facilities 38 and then exhausted to the atmosphere.

In most prior art processes, the processes are controlled relative to the quantity of the second stream component (the non-soluble carbonaceous liquid) produced per unit time. This is because it has been believed that most, if not all, of the contaminated materials removed in an in situ process are removed from the extraction wells 14 as non-soluble carbonaceous material. This is especially true with respect to in situ processes wherein the primary contaminant is a heavy organic material, such as dense non-aqueous phase liquids ("DNAPLs").

The applicants, however, have discovered that, even with respect to in situ processes wherein the primary contaminants are heavy organic materials, a very significant portion of the contaminants removed in the process is removed as materials other than non-soluble carbonaceous materials. Accordingly, in the process of the invention, each of the contaminated components removed from the extraction wells is tested for carbonaceous materials, and the in situ treatment process is thereafter controlled by the summation of the carbonaceous materials.

The analyzing of these several contaminated streams is illustrated in FIG. 2. Carbonaceous material within the first liquid stream component ($C_d$) is analyzed at a first liquid stream component analysis point 39 by a first liquid stream component analyzer 40. The results of the analysis are then passed to a control station 42. Similarly, carbonaceous material within the second liquid stream component ($C_n$) is analyzed at a second liquid stream component analysis point 44 by a second liquid stream component analyzer 46. The results of that analysis are also passed along to the control station 42.

Also in the example illustrated in FIG. 2, the carbonaceous material within the vapor stream ($C_v$) is analyzed at a vapor stream analysis point 48 by a vapor stream analyzer 50 and the results are passed along to the control station 42. It has been found that in many in situ remediation processes, a significant amount of subsurface contaminant material is removed from the subsurface formation 10 as non-condensible gases. It has been further discovered by the applicants that in many in situ remediation processes, a significant portion of the recovered contaminants are recovered in the form of carbon dioxide and other light carbon-containing gases. This fact was previously unappreciated by those skilled in the art. In evaluating the true measure of contaminants recovered from the subsurface formation 10 as carbon dioxide, the "background" amounts of naturally occurring carbon dioxide and light carbon-containing gases ($C_g$) within the subsurface formation 10 must be taken into account. The true value of the contaminant material recovered as carbon dioxide and light carbon-continuing gases is the total quantity of carbonaceous materials in the vapor stream ($C_v$) less the quantity of carbonaceous materials in the vapor stream attributable to carbonaceous materials in the subsurface formation 10 other than the targeted organic contaminants ($C_g$).

At the control station 42, each of the analysis inputs can be summed to yield a control parameter ($C_c$) representing the total organic contaminant carbonaceous materials recovered in the in situ process per unit time by the formula $C_c = C_d + C_a + C_v - C_g$.

In many applications, the control station 42 can comprise a general purpose computer 52 capable of producing a report 54 at least regarding $C_d$ and $C_v$, and ideally, regarding $C_c$. Alternatively, the control station 42 can be manned solely by a human being who reviews each of the analysis data streams from the three analyzers and controls the in situ treatment process pursuant to the results indicated by those analysis streams.

In a typical in situ operation, such as that which is illustrated in FIG. 1, the in situ process is controlled by increasing or decreasing the amount of steam injected into the subsurface formation 10 and/or by increasing or decreasing the vacuum drawn on the extraction conduits 14. In more complex in situ processes, wherein the temperature gradient across the entire contaminated zone 6 is monitored, the steam input to one or more specific injection wells 12 can be increased or decreased and/or the amount of vacuum in one or more of the individual extraction wells 14 can be increased or decreased. In remediation processes which entail the injection of an oxidant into the contaminated zone 6 and/or the periodic introduction of enzymatic agents into the contaminated zone 6, the controlling of the processes may also include the increasing or decreasing of the input of such oxidants and/or enzymatic agents.

Since the method of the invention allows the control of the in situ process pursuant to virtually the entirety of the contaminated materials recovered from the process in the form of various species of carbonaceous materials, the in situ process is controlled with a much greater degree of accuracy and efficiency.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. A continuous process for removing organic contaminants from a subsurface formation comprising the steps of:

(a) treating the subsurface formation to mobilize the organic contaminants, said treating of the subsurface formation including withdrawing from the subsurface formation a liquid stream and a vapor stream, the liquid stream containing water, dissolved carbonaceous material and non-dissolved carbonaceous material;

(b) separating the liquid stream into a first liquid stream component comprised substantially of water and soluble carbonaceous material and a second liquid stream component comprised substantially of non-soluble carbonaceous material;

(c) testing the first liquid component stream to determine $C_d$, where $C_d$ is the amount of carbonaceous material in the first liquid stream component produced per unit of time by the treating of the subsurface formation in step (a);

(d) testing the second liquid stream component to determine $C_n$, where $C_n$ is the amount of carbonaceous material in the second liquid stream component produced per unit of time by the treating of the subsurface formation in step (a);

(e) testing the vapor stream to determine $C_v$, where $C_v$ is the amount of carbonaceous material in the vapor stream produced per unit of time by the treating of the subsurface formation in (a);

(f) determining $C_g$, where $C_g$ is the quantity of carbonaceous materials in the vapor stream produced per unit of time by the treating of the subsurface formation in step (a), which is attributable to carbonaceous material in the subsurface formation other than the organic contaminants;

(g) computing $C_c$, where $C_c = C_d + C_n + C_v - C_g$;

(h) controlling the treating of the subsurface formation in step (a) using $C_c$.

2. The process of claim 1 wherein the computing of $C_c$ in step (g) is performed using a digital computer.

3. The process of claim 2 wherein the computer produces a report regarding at least $C_d$.

4. The process of claim 1 wherein the treating of the subsurface formation in step (a) includes heating the subsurface formation to mobilize the organic contaminants.

5. The process of claim 1 wherein the treating of the subsurface formation in step (a) includes heating the subsurface formation with steam to mobilize the organic contaminants.

6. The process of claim 1 wherein the withdrawing of a vapor stream from the subsurface formation in step (a) is carried out by withdrawing the vapor stream via a perforated extraction conduit maintained under vacuum.

7. The process of claim 1 wherein the treating of the subsurface formation in step (a) includes the heating of the subsurface formation to a temperature between about 100° C. and about 160° C.

* * * * *